US011214841B2

(12) United States Patent
Green

(10) Patent No.: US 11,214,841 B2

(45) Date of Patent: Jan. 4, 2022

(54) RAPID LOW-COST DETECTION OF VALLEY FEVER USING ISOTHERMAL AMPLIFICATION AND SENSING METHODS

(71) Applicant: Arizona Board of Regents on behalf of Arizona State University, Scottsdale, AZ (US)

(72) Inventor: Alexander Green, Scottsdale, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 349 days.

(21) Appl. No.: 16/294,578

(22) Filed: Mar. 6, 2019

(65) Prior Publication Data

US 2019/0276901 A1 Sep. 12, 2019

Related U.S. Application Data

(60) Provisional application No. 62/639,623, filed on Mar. 7, 2018.

(51) Int. Cl.

*C12Q 1/6895* (2018.01)
*C12Q 1/6837* (2018.01)
*C12Q 1/6897* (2018.01)

(52) U.S. Cl.

CPC ......... *C12Q 1/6895* (2013.01); *C12Q 1/6837* (2013.01); *C12Q 1/6897* (2013.01)

(58) Field of Classification Search

CPC .................................................... C12Q 1/6895

See application file for complete search history.

(56) References Cited

U.S. PATENT DOCUMENTS

| | | | |
|---|---|---|---|
| 5,580,971 | A | 12/1996 | Mitsuhashi |
| 2019/0071737 | A1 | 3/2019 | Green |
| 2019/0218624 | A1 | 7/2019 | Green |
| 2019/0256898 | A1 | 8/2019 | Green |
| 2019/0285620 | A1 | 9/2019 | Green |
| 2019/0382746 | A1 | 12/2019 | Green |

FOREIGN PATENT DOCUMENTS

| | | | |
|---|---|---|---|
| WO | 2017147585 | A1 | 8/2017 |
| WO | 2017205668 | A1 | 11/2017 |
| WO | 2018026762 | A1 | 2/2018 |
| WO | 2018026765 | A1 | 2/2018 |
| WO | 2018027177 | A1 | 2/2018 |
| WO | 2018075502 | A1 | 4/2018 |
| WO | 2018093898 | A1 | 5/2018 |
| WO | 2018112350 | A1 | 6/2018 |
| WO | 2018187687 | A1 | 10/2018 |

OTHER PUBLICATIONS

Sakai, K. et al., Identification of Fungal Pathogens by Visivle Microarray System in Combination with Isothermal Gene Aplification, Mycopathologia, vol. 178, pp. 11-26 (Year: 2014).*

Ampel, N. M. "The diagnosis of coccidioidomycosis." F1000 medicine reports 2 (2010).

Bialek, R., et al. "PCR assays for identification of Coccidioides posadasii based on the nucleotide sequence of the antigen 2/proline-rich antigen." Journal of clinical microbiology 42.2 (2004): 778-783.

Binnicker, M. J., et al. "Detection of Coccidioides species in clinical specimens by real-time PCR." Journal of clinical microbiology 45.1 (2007): 173-178.

Chiller, T.M., et al., "Coccidioidomycosis," Infectious disease clinics of North America 17, 41-57, viii (2003).

De Aguiar Cordeiro, R., et al. "Rapid diagnosis of coccidioidomycosis by nested PCR assay of sputum." Clinical microbiology and infection 13.4 (2007): 449-451.

De Macedo, R. CL, et al. "Molecular identification of *Coccidioides* spp. in soil samples from Brazil." BMC microbiology 11.1 (2011): 108.

Deiman, B., et al. "Characteristics and applications of nucleic acid sequence-based amplification (NASBA)." Molecular biotechnology 20.2 (2002): 163-179.

Dicaudo, D. J. "Coccidioidomycosis: a review and update." Journal of the American Academy of Dermatology 55.6 (2006): 929-942.; quiz 943-925 (2006).

Filonov, G.S. et al., "Broccoli: Rapid Selection of an RNA Mimic of Green Fluorescent Protein by Fluorescence-Based Selection and Directed Evolution," Journal of the American Chemical Society 136, 16299-16308 (2014).

Galgiani, J. N., et al. "Coccidioidomycosis." Clinical Infectious Diseases 41.9 (2005): 1217-1223.

Green, A. A., et al. "Toehold switches: de-novo-designed regulators of gene expression." Cell 159.4 (2014): 925-939.

Li, J. et al. "Advances in isothermal amplification: novel strategies inspired by biological processes." Biosensors and Bioelectronics 64 (2015): 196-211.

Navalkar, K. A., et al. "Application of immunosignatures for diagnosis of valley fever." Clin. Vaccine Immunol. 21.8 (2014): 1169-1177.

Pardee, K., et al. (2014). Paper-based synthetic gene networks. Cell, 159(4), 940-954.

Pardee, K., et al. "Rapid, low-cost detection of Zika virus using programmable biomolecular components." Cell 165.5 (2016): 1255-1266.

Piepenburg, O., et al., "DNA detection using recombination proteins," PLoS Biology 4, e204 (2006).

Sema, M. et al., "Evaluation of non-instrumented nucleic acid amplification by loop-mediated isothermal amplification (NINA-LAMP) for the diagnosis of malaria in Northwest Ethiopia," Malaria Journal 14, 1-9 (2015).

Stevens, D.A., et al. "Expert opinion: what to do when there is Coccidioides exposure in a laboratory." Clinical infectious diseases 49.6 (2009): 919-923.

(Continued)

*Primary Examiner* — Teresa E Strzelecka

(74) *Attorney, Agent, or Firm* — Quarles & Brady LLP

(57) ABSTRACT

Provided herein are methods and compositions for rapid, highly sensitive detection of Valley fever in biological samples. In particular, provided herein is a low-cost method for detecting Valley fever that provides reliable, visible test results and does not require elaborate biosafety precautions or sophisticated laboratory equipment.

14 Claims, 8 Drawing Sheets

Specification includes a Sequence Listing.

(56) References Cited

OTHER PUBLICATIONS

Sun, Z. Z., et al. "Protocols for implementing an *Escherichia coli* based TX-TL cell-free expression system for synthetic biology." JoVE (Journal of Visualized Experiments) 79 (2013): e50762.
Torres, C., et al., "LAVA: An Open-Source Approach To Designing LAMP (Loop-Mediated Isothermal Amplification) DNA Signatures," BMC Bioinformatics 12, 1-7 (2011).
Tsang, C. A., et al. "Enhanced surveillance of coccidioidomycosis, Arizona, USA, 2007-2008." Emerging infectious diseases 16.11 (2010): 1738.
Wahyuningsih, R., et al. "Simple and rapid detection of Candida albicans DNA in serum by PCR for diagnosis of invasive candidiasis." Journal of clinical microbiology 38.8 (2000): 3016-3021.
Welsh, O., et al. "Coccidioidomycosis." Clinics in dermatology 30.6 (2012): 573-591.
Zadeh, J. N., et al. "NUPACK: analysis and design of nucleic acid systems." Journal of computational chemistry 32.1 (2011): 170-173.
U.S. Appl. No. 16/303,937.
U.S. Appl. No. 16/322,719.
U.S. Appl. No. 16/322,799.
U.S. Appl. No. 16/349,752.
U.S. Appl. No. 16/468,846.
U.S. Appl. No. 16/603,338.

* cited by examiner

RAPID LOW-COST DETECTION OF VALLEY FEVER USING ISOTHERMAL AMPLIFICATION AND SENSING METHODS

CROSS-REFERENCE TO RELATED APPLICATIONS

This application claims priority to U.S. Provisional Application No. 62/639,623, filed Mar. 7, 2018, which is hereby incorporated by reference in its entirety for all purposes.

STATEMENT REGARDING FEDERALLY FUNDED RESEARCH OR DEVELOPMENT

This invention was made with government support under GM126892 awarded by the National Institutes of Health. The government has certain rights in the invention.

BACKGROUND

Valley fever or coccidioidomycosis is a systemic fungal infection that is endemic to the Southwestern United States and occurs with the highest frequency in the state of Arizona, with over 50,000 reported cases from 2010 to 2014 according to the CDC. The illness is caused by two different fungal species: *Coccidioides immitis*, which is limited to California's San Joaquin valley; and *Coccidioides posadasii*, which is distributed throughout semi-arid regions in the U.S., Mexico, and Central and South America. Although the two species are genetically distinct, both cause very similar symptoms in infected patients.

Valley fever is currently detected through three principal methods in the United States: culture, microscopy, and serology. Both species of *Coccidioides* grow readily in culture media at 35° C. and can be detected in 2-7 days. Cells from the culture can then be identified in microscopy through their appearance. Alternatively, chemiluminescent nucleic acid probes (AccuProbe, Hologic, Inc.) that target ribosomal RNAs (rRNAs) of the fungi can be used for more specific molecular identification. Beyond the time required for the assay, the critical drawback of these diagnostic methods is the danger associated with culturing *Coccidioides*. These fungi were listed as Select Agents of bioterrorism up until 2012 and require biosafety level 3 containment. When cultured to substantial quantities, *Coccidioides* species pose a significant risk for unintended infection for laboratory workers. Microscopy can be applied directly to respiratory samples for identification albeit with poor sensitivity. Serology is currently the most commonly used method of detecting Valley fever using immunodiffusion assays. These assays provide sensitivity ranging from 75 to 91%. However, they can yield false negatives, particularly in immunocompromised patients who are unable to mount an effective immune response.

Survey of conventional diagnostics currently approved for use in the United States reveals that they pose substantial safety concerns to laboratory workers and require multiple days to return results, or they offer poor sensitivity, particularly for immunocompromised patients most likely to suffer through serious bouts of the illness. Of the diagnostics in development, PCR- and immunosignature-based assays are highly sensitive and can be specific; however, they require substantial investment in equipment and trained personnel for running the tests. These infrastructure requirements substantially increase both the cost and time required to return assay results. Accordingly, there remains a need in the art for rapid, inexpensive, and highly sensitive diagnostic tests for Valley fever that require neither sophisticated laboratory equipment nor biosafety level 3 containment.

SUMMARY

This disclosure is related to methods and compositions for rapid, highly sensitive detection of the causative agents of Valley fever. As described herein, the methods and compositions are useful for early detection of Valley fever and, consequently, improved health outcomes.

In a first aspect, provided herein is a method of detecting a target Valley Fever (VF) nucleic acid in a sample. The method can comprise or consist essentially of the steps of (a) amplifying nucleic acids obtained from a biological sample of a subject, wherein amplifying comprises isothermal amplification; (b) contacting the amplified nucleic acid to a toehold switch, wherein the toehold switch encodes at least a portion of a reporter protein and comprises one or more single-stranded toehold sequence domains that are complementary to a target VF nucleic acid or the reverse complement thereof, wherein the contacting occurs under conditions that allow translation of the coding domain in the presence of the target nucleic acid but not in the absence of the target nucleic acid; and (c) detecting the reporter protein as an indicator that the target VF nucleic acid is present in the amplified nucleic acids. The target VF nucleic acid can be a *C. immitis* DNA or a *C. posadasii* DNA. The target nucleic acid can detectable at a concentration as low as 1 fM. The reporter protein, if present, can be detectable in less than 4 hours. The reporter protein, if present, can be detectable in less than 2 hours. The isothermal amplification can be a method selected from the group consisting of NASBA, LAMP, and RPA. The toehold switch can comprise SEQ ID NO:1.

In another aspect, provided herein is a method of detecting presence of pathogen-associated nucleic acid in a sample. The method can comprise or consist essentially of the steps of: (a) amplifying nucleic acids obtained from a biological sample of a subject, wherein amplifying comprises isothermal amplification; and (b) contacting the amplified nucleic acids to an aptamer-based sensor, wherein the aptamer-based sensor is a nucleic acid sequence comprising one or more single-stranded toehold sequence domains that are complementary to the target Valley Fever-associated nucleic acid, a fully or partially double-stranded stem domain, a loop domain, and an aptamer-ligand complex, and wherein the contacting occurs under conditions that promote activation of the aptamer-ligand complex in the presence of the target Valley Fever-associated nucleic acid but not in the absence of the Valley Fever-associated nucleic acid. The aptamer-ligand complex can comprise a fluorescent aptamer selected from the group consisting of Broccoli, Spinach2, Carrot, Radish, a G-quadruplex-containing aptamer, and a malachite green binding aptamer. Fluorescence, if present, can be detectable in less than 4 hours. Fluorescence, if present, can be detectable in less than 2 hours. The target VF nucleic acid can be a *C. immitis* DNA or a *C. posadasii* DNA. The isothermal amplification can be method selected from the group consisting of NASBA, LAMP, and RPA. The target nucleic acid can be detectable at a concentration as low as 1 fM.

In a further aspect, provided herein is a synthetic Valley Fever (VF)-specific toehold switch sensor comprising a fully or partially double-stranded stem domain, a loop domain, a toehold domain, and at least a portion of a coding sequence of a reporter gene, wherein the toehold domain and at least a portion of the stem domain are complementary to a target VF RNA sequence. The toehold switch sensor can comprise the RNA sequence of SEQ ID NO:1.

In another aspect, provided herein is a device for identifying a Valley Fever (VF)-associated nucleic acid, comprising a preserved paper test article, wherein the method is performed using the preserved paper test article. The paper test article can be preserved by freeze-drying.

In a further aspect, provided herein is a kit for detecting a Valley Fever (VF)-associated nucleic acid, comprising a plurality of preserved test articles, a VF detection agent, a plurality of toehold switches that encode at least a portion of a reporter protein and comprise one or more single-stranded toehold sequence domains that are complementary to a target VF nucleic acid or the reverse complement thereof, and an electronic optical reader. Also provided herein is a kit for detecting a Valley Fever (VF)-associated nucleic acid, comprising a plurality of aptamer-based sensors and an electronic optical reader, wherein the aptamer-based sensor is a nucleic acid sequence comprising one or more single-stranded toehold sequence domains that are complementary to the target Valley Fever-associated nucleic acid, a fully or partially double-stranded stem domain, a loop domain, and an aptamer-ligand complex. The kit may further comprise instructions for performing a detection method as described herein.

DETAILED DESCRIPTION

All publications, including but not limited to patents and patent applications, cited in this specification are herein incorporated by reference as though set forth in their entirety in the present application.

The methods and compositions provided herein are based at least in part on the inventors' development of a rapid, highly sensitive assay for detecting the causative agents of Valley fever in biological samples. Advantages of the methods and compositions provided herein are multifold. For example, results can be obtained in under 4 hours, and the assays require limited laboratory infrastructure (i.e., pipettes, hot plate, two heating blocks). Consequently, they do not need to take place at centralized labs and can provide same-day results for patients who are in desperate need of care. Second, the assays are nucleic acid based so they can provide improved specificity over antibody-based tests and can be rapidly repurposed for other pathogens, for instance if a new, more virulent *Coccidioides* strain emerges. Third, they are extremely low cost at $1 per test presently and potential for scaling down to ~$0.10 per test, and they do not require a cold-chain. This technology could substantially reduce overall costs for Valley fever testing in affected states and improve patient outcomes. Fourth, the liquid-based reactions in which amplification and detection are combined in a single test tube enable rapid detection of Valley fever using aptasensors. Tests results with aptasensors can be detected by eye using simple and low-cost instrumentation.

Figure 1:
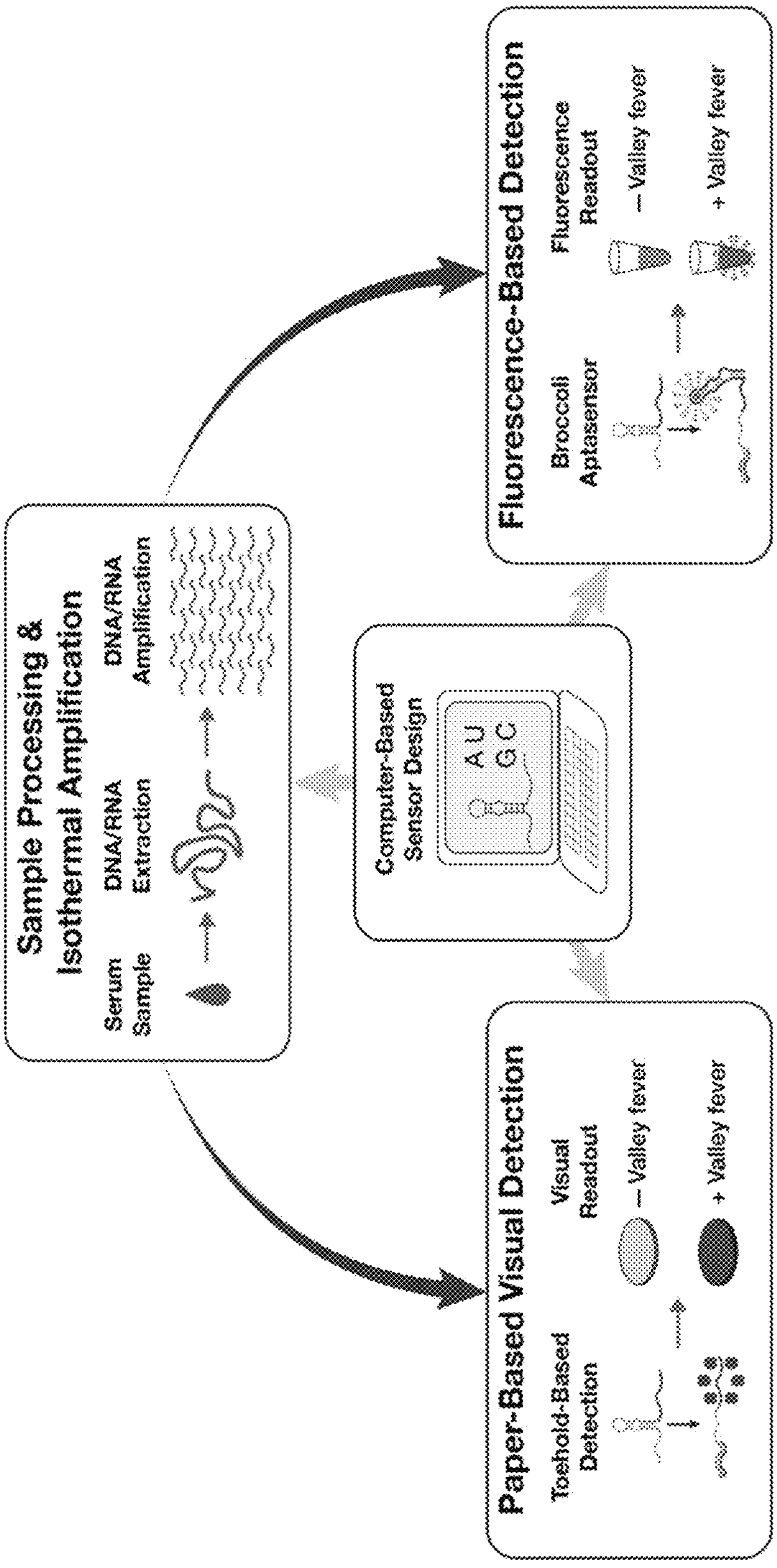
FIG. 1 is a schematic illustrating a protocol for screening serum samples for potential Valley fever infections. Serum samples from patients with potential Valley fever infections will be subject to a simple DNA/RNA extraction procedure, such as a brief boiling step, and amplified using isothermal amplification methods, such as recombinase polymerase amplification (RPA), nucleic acid sequence-based amplification (NASBA), or loop-mediated isothermal amplification (LAMP). The resulting amplified nucleic acids will then be detected using either cell-free reactions using nucleic-acid-sensing riboregulators, such as toehold switches or loop-mediated riboregulators; or using aptasensor systems with fluorescent readout, such as the Broccoli aptasensor system. The former detection reactions can be deployed in paper-based cell-free systems and use a colorimetric reporter for a test result easily seen by eye. The latter detection reactions can employ one-pot amplification and detection reactions to increase speed, and they produce a strong fluorescent output that can be detected by eye using simple, cost-effective instrumentation. Computer-based design is used to generate high-performance sensors and companion amplification primers to speed the diagnostic development process.

Accordingly, in a first aspect, provided herein are two diagnostic platforms for detecting a Valley Fever-specific nucleic acids (e.g., *Coccidioides posadasii* DNAs, *Coccidioides immitis* DNAs) in a sample. As illustrated in FIG. 1, both platforms use DNA and RNA extracted from patient serum samples and amplified using isothermal amplification reactions.

Methods of the first platform can comprise or consist essentially of the following steps: (a) amplifying nucleic acids obtained from a biological sample of a subject, wherein amplifying comprises isothermal amplification; (b) contacting the amplified nucleic acid to a toehold switch, wherein the toehold switch encodes at least a portion of a reporter protein and comprises one or more single-stranded toehold sequence domains that are complementary to a target VF nucleic acid or the reverse complement thereof, wherein the contacting occurs under conditions that allow translation of the coding domain in the presence of the target nucleic acid but not in the absence of the target nucleic acid; and (c) detecting the reporter protein as an indicator that the target VF nucleic acid is present in the amplified nucleic acids.

Figures 2A, 2B:
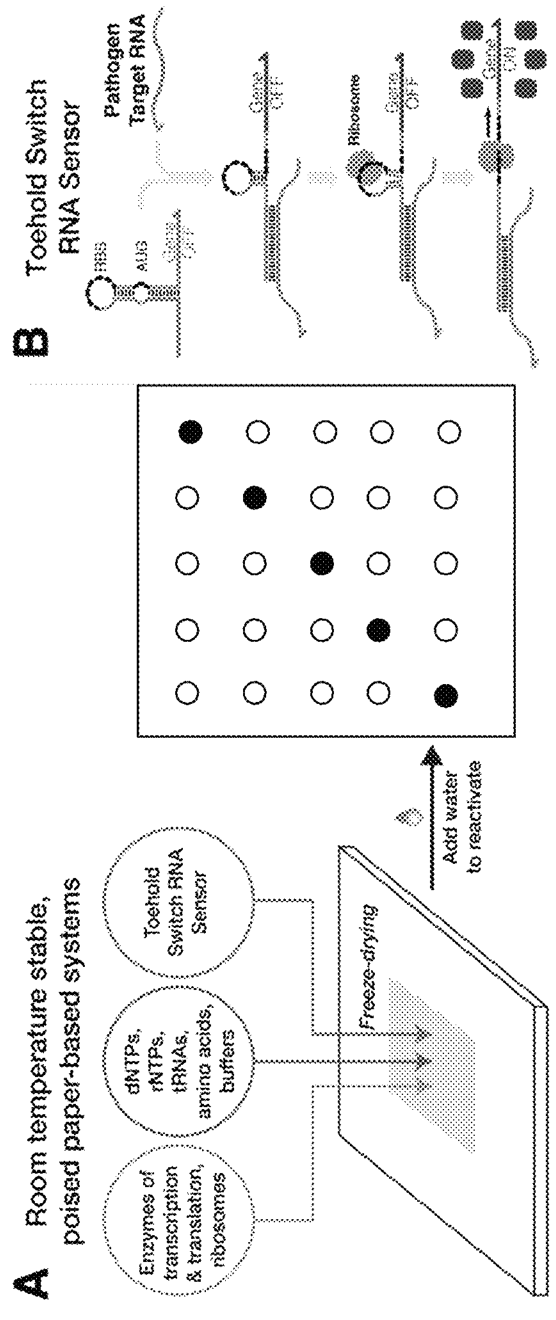
FIGS. 2A-2B are schematic illustrations of the detection modality employing paper-based cell-free reactions and toehold switch RNA sensors. (A) Paper-based cell-free systems employ freeze-drying to preserve cell-free reactions for extended periods of time on stable, easily distributed porous media. At the point of use, the cell-free systems can be reactivated by adding water and the embedded toehold switch nucleic acid sensors can be used for DNA/RNA detection. These reactions provide a simple colorimetric test readout. (B) Schematic of the toehold switch RNA sensors used for these Valley fever diagnostics. This toehold switch design was first reported for detection of the Zika virus and employs a conserved upper stem domain and does not require a downstream RNA refolding domain for detection of natural RNA/DNA sequences.
Figures 3A, 3B, 3C:
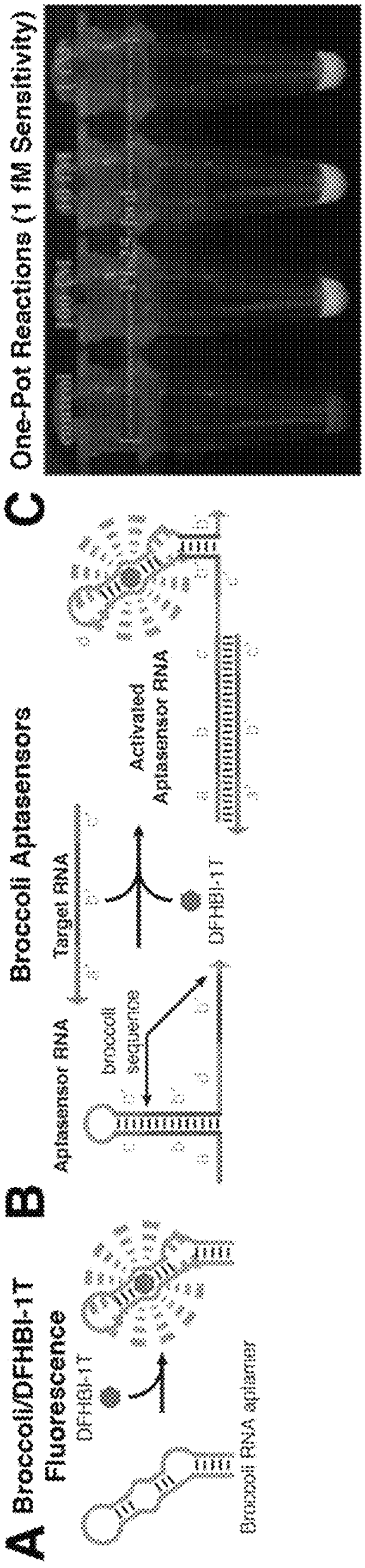
FIGS. 3A-3C illustrate aptasensor detection schemes based on the Broccoli aptamer. (A) The Broccoli RNA aptamer binds to the conditional fluorophore DFHBI-1T. Upon binding the initially non-fluorescent DFHBI-1T becomes strongly fluorescent, emitting green light. (B) The design of the Broccoli aptasensor. The aptasensor contains the complete sequence for the Broccoli aptamer, however, it is unable to fold because of an upstream hairpin secondary structure. Upon binding of the target RNA (or DNA) through a toehold-mediated interaction, the inhibitory secondary structure is released and the Broccoli aptamer can fold into its active structure. The properly folded aptamer can then bind to the conditional fluorophore DFHBI-1T and activate its strong green fluorescence. (C) Photograph of one-pot amplification and detection reactions using the Broccoli sensor and the NASBA isothermal amplification reaction. These diagnostics can detect RNAs down to a concentration of 1 fM and provide visible fluorescence using suitable light and filter combinations.

In certain embodiments, the method employs programmable riboregulators known as toehold switches. As used herein, the term "toehold switch" generally refers to a nucleic acid-based regulator of gene expression, configured to repress or activate translation of an open reading frame and thus production of a protein. Toehold switches, which are a type of prokaryotic riboregulator, activate gene expression in response to cognate RNAs with essentially arbitrary sequences. Gene regulation is achieved through the presence of a regulatory nucleic acid element (the cis-repressive RNA or crRNA) within the 5' untranslated region (5' UTR) of an mRNA molecule. The cis-repressive nucleic acid element (crRNA) forms a hairpin structure comprising a stem domain and a loop domain through complementary base pairing. The hairpin structure blocks access to the mRNA transcript by the ribosome, thereby preventing translation. In some embodiments, the stem domain of the hairpin structure sequesters the ribosome binding site (RBS). In some embodiments, including, for example, embodiments involving eukaryotic cells, the stem domain of the hairpin structure is positioned upstream of the start (or initiation) codon. As described in the Examples, that follow, toehold switches particularly useful for the methods provided herein are configured for lower leakage relative to previously described riboregulators. As illustrated in FIG. 2A, binding of a cognate target RNA to the updated toehold switch unwinds the lower half of the switch RNA hairpin and leaves the conserved upper stem-loop intact. This upper stem-loop is sufficiently weak to expose the RBS to enable translation to occur. Unlike earlier toehold switch mRNA sensors, the updated systems do not employ an RNA refolding domain downstream of the start codon, which could hamper translation of the output gene.

In some cases, toehold switches are synthetic (engineered) molecules. In other cases, toehold switches comprise endogenous, naturally occurring RNAs or regions thereof. See, for example, U.S. 2015/0275203. The stem domain can be as small as 12 bps, but in some cases will be longer than 12 bps, including 13, 14, 15, 16, 17, 18, 19, 20, or more base pairs in length. In other cases, the loop domain is complementary to a non-naturally occurring RNA. The toehold domain can be 5, 6, 7, 8, 9, 10, 11, 12, 13, 14, 15, 16, 17, 18, 19, 20, or more nucleotides in length.

The toehold switch further comprises a fully or partially double-stranded stem domain comprising an initiation codon, a loop domain comprising a RBS, and a coding domain. The unpaired region upstream of the RBS in a toehold switch can be shortened or lengthened to modulate protein output and, in turn, device dynamic range. In some cases, the toehold and stem domains are complementary in sequence to a naturally occurring RNA. In other cases, the sequence detected can also be the complement of the naturally occurring RNA. For example, after isothermal amplification, it is possible to transcribe the antisense of the RNA rather than the sense.

The toehold switch can further comprise a thermodynamically stable double-stranded stem domain, a loop domain comprising a ribosome binding site, and a coding domain. Preferably, the loop domain is 11 nucleotides or 12 nucleotides in length. In some cases, the length of loop domains can be increased or decreased, for example, to alter reaction thermodynamics.

In certain embodiments, the toehold switch is configured to detect a portion of a pathogen genome that is conserved among two or more species or strains of the pathogen. For example, the Examples that follow describe identifying conserved sequence regions of Valley Fever specific nucleic acids suitable for isothermal amplification and toehold-switch-based detection. In some cases, toehold switches useful for the methods provided herein include, without limitation, synthetic norovirus-specific toehold switches that comprise a fully or partially double-stranded stem domain, a loop domain, a toehold domain, and at least a portion of a coding sequence of a reporter gene, wherein the toehold domain and at least a portion of the stem domain are complementary to a target norovirus RNA sequence. In some cases, synthetic Valley Fever-specific toehold switches comprise RNA sequence set forth as SEQ ID NO:1.

In another aspect, provided herein is a method of detecting presence of pathogen-associated nucleic acid in a sample. The method can comprise or consist essentially of the following steps: (a) amplifying nucleic acids obtained from a biological sample of a subject, wherein amplifying comprises isothermal amplification; and (b) contacting the amplified nucleic acids to an aptamer-based sensor, wherein the aptamer-based sensor is a nucleic acid sequence comprising one or more single-stranded toehold sequence domains that are complementary to the target Valley Fever-associated nucleic acid, a fully or partially double-stranded stem domain, a loop domain, and an aptamer-ligand complex, and wherein the contacting occurs under conditions that promote activation of the aptamer-ligand complex in the presence of the target Valley Fever-associated nucleic acid but not in the absence of the Valley Fever-associated nucleic acid.

In certain embodiments, aptasensors suitable for the methods described herein comprise aptamers that can bind to conditionally fluorescent dye molecules (e.g., Broccoli/DFHBI-1T). See FIG. 1 and FIGS. 3A-3C. The Broccoli/DFHBI-1T system is ideal for aptasensor studies since triggered formation of the aptamer results in detectable fluorescence from cells. Aptamer-based sensors trigger the formation of functional aptamers in response to the binding of target nucleic acids. As used herein, the terms "aptamer-based sensors" and "aptasensor" refer to molecular sensors that bind to a target analyte (e.g. a nucleic acid) and refold into an active ("ON") state aptamer structure. As used herein, the term "aptamer" refers to nucleic acids or peptide molecules that are capable to bind a specific target. In particular, aptamers can comprise single-stranded (ss) oligonucleotides and peptides, including chemically synthesized peptides. Nucleic acids generally refer to polymers comprising nucleotides or nucleotide analogs joined together through backbone linkages such as but not limited to phosphodiester bonds. Nucleic acids include deoxyribonucleic acids (DNA) and ribonucleic acids (RNA) such as messenger RNA (mRNA), transfer RNA (tRNA), etc.

Any appropriate fluorescent aptamer can be used for aptamer-based sensors ("aptasensors") described herein. For example, the fluorescent RNA aptamer can be Broccoli. As used herein, the term "Broccoli" or "Broccoli aptamer" refers to a 49-nt fluorescent RNA aptamer-fluorophore complex (see Filonov et al., *J. Am. Chem. Soc.* 2014, 136(46):16299-16308) that confers fluorescence to a target analyte (e.g., target RNA) of interest via activation of the bound fluorophore DFHBI or a DFHBI-derived fluorophore such as (Z)-4-(3,5-difluoro-4-hydroxybenzylidene)-2-methyl-1-(2,2,2-trifluoroethyl)-1H-imidazol-5(4H)-one) (DFHBI-1T) as described by Song et al., *J. Am. Chem. Soc.* 2014, 136:1198. Other fluorescent RNA aptamers that can be used include, without limitation, Spinach and Spinach2 (Strack et al., *Nature Methods* 2013, 10:1219-1224), Carrot and Radish (Paige et al., *Science* 2011, 333:642-646), RT aptamer (Sato et al., *Angew. Chem. Int. Ed.* 2014, 54:1855-1858), hemin-binding G-quadruplex DNA and RNA aptamers, and malachite green binding aptamer (Babendure et al., *J. Am. Chem. Soc.* 2003). Several new alternatives to the Broccoli aptamer were recently reported by Song et al., *Nature Chemical Biology* 13, 1187 (2017). These aptamers all bind to the molecule 3,5-difluoro-4-hydroxybenzylidene-imidazolinone-2-oxime (DFHO), which resembles the fluorophore of red fluorescent protein (RFP), and thus provide red-shifted fluorescence compared to the green emission from Broccoli when it binds to DFHBI-1T. The new DFHO-binding aptamers are named Corn, Red Broccoli, and Orange Broccoli. As will be understood by practitioners in the art, selection of a fluorescent RNA aptamer-fluorophore complex for use in an aptasensor described herein will depend on fundamental properties of the aptamer such as brightness (or enzymatic output), folding properties, and amenability to sequence modifications.

In other cases, the aptasensors provided herein comprise colorimetric aptamers. In such cases, the presence and location of the target nucleic acid is indicated by a color change. Any appropriate colorimetric aptamer can be used. The term "colorimetric" is defined as an analysis where the reagent or reagents constituting the aptasensors system produce a color change in the presence or absence of an analyte. The degree the color changes in response to the analyte (e.g., target nucleic acid) may be quantified by colorimetric quantification methods known to those of ordinary skill in the art in. In some cases, standards containing known amounts of the selected analyte may be analyzed in addition to the sample to increase the accuracy of the comparison.

An advantage of the methods described herein is that they can be applied for the detection and identification of essentially any nucleic acid-containing organism. Accordingly, the pathogen can be virtually any pathogen or infectious agent (e.g., viruses, parasites, bacteria, fungi, prions) for which genetic information is available.

The term "detect" or "detection" as used herein indicates the determination of the existence, presence or fact of a target or signal in a limited portion of space, including but not limited to a sample, a reaction mixture, a molecular complex and a substrate including a platform and an array. Detection is "quantitative" when it refers, relates to, or involves the measurement of quantity or amount of the target or signal (also referred as quantitation), which includes but is not limited to any analysis designed to determine the amounts or proportions of the target or signal. Detection is "qualitative" when it refers, relates to, or involves identification of a quality or kind of the target or signal in terms of relative abundance to another target or signal, which is not quantified. An "optical detection" indicates detection performed through visually detectable signals: fluorescence, spectra, or images from a target of interest or a probe attached to the target.

In some cases, the method includes detecting pathogen-associated nucleic acids in a biological sample obtained from a subject, where identifying comprises: (i) amplifying nucleic acid obtained from the biological sample; (ii) contacting the amplified nucleic acid of (i) to a unimolecular aptamer-based sensor under conditions that allow for sequence-specific activation of the aptamer-based sensor when a pathogen-specific nucleic acid is present; and (iii) detecting activation of the aptamer-based sensor by detecting fluorescence of the bound fluorophore, where fluorescence is not detectable in the absence of the pathogen-specific target nucleic acid, thereby indicating the presence of the pathogen-specific nucleic acid.

As shown in FIG. 1 and FIG. 2B, the toehold switch can be operably linked to a reporter element (e.g., at least a portion of an *E. coli* lacZ reporter element encoding β-galactosidase) that is 3' to the hairpin structure. As used herein, the term "operably linked" refers to a relationship between two nucleic acid sequences wherein the production or expression of one of the nucleic acid sequences is controlled by, regulated by, modulated by, etc., the other nucleic acid sequence. Reporter proteins appropriate for the methods provided herein include, without limitation, enzymatic reporters (e.g., β-galactosidase, alkaline phosphatase, DHFR, CAT), fluorescent or chemiluminescent reporters (e.g., GFP variants, mCherry, luciferase, e.g., luciferase derived from the firefly (*Photinus pyralis*) or the sea pansy (*Renilla reniformis*) and mutants thereof), etc.

Any isothermal amplification protocol can be used according to the methods provided herein. In some cases, isothermal amplification comprises NASBA (nucleic acid sequence-based amplification). Other isothermal amplification methods include: loop-mediated isothermal amplification (LAMP), strand displacement amplification (SDA), helicase-dependent amplification (HDA), nicking enzyme amplification reaction (NEAR), signal mediated amplification of RNA technology (SMART), rolling circle amplification (RCA), isothermal multiple displacement amplification (IMDA), single primer isothermal amplification (SPIA), recombinase polymerase amplification (RPA), and polymerase spiral reaction (PSR), which is described at nature.com/articles/srep12723 on the World Wide Web. In some cases, recombinase polymerase amplification (RPA) is used with the "one-pot" amplification and detection methods provided herein. In such cases, the methods comprise performing reverse transcription (RT), RPA, and transcription (TX) methods in a single test tube. In other cases, LAMP (loop-mediated isothermal amplification) is performed. As described in the Examples that follow, the unimolecular aptamer-based sensors described herein can bind directly to DNA LAMP amplification products. Alternatively, the amplification protocol is configured to add promoter sites to DNA LAMP amplification products such that each LAMP DNA can generate multiple RNA copies for improved assay effectiveness.

Nucleic acids and/or other moieties of the invention may be isolated. As used herein, "isolated" means to separate from at least some of the components with which it is usually associated whether it is derived from a naturally occurring source or made synthetically, in whole or in part.

Nucleic acids and/or other moieties of the invention may be purified. As used herein, purified means separate from the majority of other compounds or entities. A compound or moiety may be partially purified or substantially purified. Purity may be denoted by a weight by weight measure and may be determined using a variety of analytical techniques such as but not limited to mass spectrometry, HPLC, etc.

In some cases, it may be advantageous to adapt the methods described herein for high-throughput, reproducible, and rapid detection, for example in a clinical setting or in the field. When aptasensor output is coupled to a reporter element, such as fluorescence emission or a color-change through enzymatic activity, the aptasensors act as genetically encodable sensors and imaging probes for endogenous virus RNAs in a sample. For example, such aptasensors can be provided in a device configured for rapid, reproducible detection in a clinical setting. In some cases, the device comprises a preserved paper test article, upon which any step(s) of the method provided herein can be performed. In some cases, the device comprises a preserved paper test article, upon which any step(s) of the method provided herein can be performed. In preferred embodiments, the paper test article is preserved by freeze-drying. In such cases, aptasensors and methods provided herein can be performed at a cost of less than $1 per assay and do not require translation to produce reporters for the diagnostic test. In other embodiments, nucleic acids encoding the aptasensors can be freeze-dried in test tubes to render them stable at room temperature. These freeze-dried components can be reactivated upon addition of a sample and water, and can report on the presence of an endogenous nucleic acid of interest in the sample.

Any appropriate sample can be used according to the methods provided herein. In some cases, the sample is a biological sample obtained from an individual (e.g., a human subject, a non-human mammal). The sample is, in some cases, a diagnostic sample. The sample type will vary depending on the target pathogen. For example, Valley Fever can be detected in serum or blood samples or in sputum samples. Accordingly, a diagnostic sample for detecting Valley Fever can be a serum sample or a blood sample or a sputum sample. In some cases, serum samples have been frozen (e.g., at −80° C.) prior to testing since freezing is known to kill *Coccidioides*. Samples appropriate for use according to the methods provided herein can also include, without limitation, food samples, drinking water, environmental samples, and agricultural products. In some cases, samples appropriate for use according to the methods provided herein are "non-biological" in whole or in part. Non-biological samples include, without limitation, plastic and packaging materials, paper, clothing fibers, and metal surfaces. In certain embodiments, the methods provided herein are used in food safety and food biosecurity applications, such as screening food products and materials used in food processing or packaging for the presence of pathogens in biological and/or non-biological samples.

Other applications for which the methods provided herein include, without limitation, profiling species in an environment (e.g., water); profiling species in an human or animal microbiome; food safety applications (e.g., detecting the presence of a pathogenic species, determining or confirming food source/origin such as type of animal or crop plant); obtaining patient expression profiles (e.g., detecting expression of a gene or panel of genes (e.g., biomarkers) to monitor the patient's response to a therapeutic regimen, to select a therapeutic regimen suitable for the patient, or to detect exposure of the patient to a toxin or environmental agent that affects expression of the gene or a panel of genes.

In some cases, the device is used with a portable electronic reader. In this manner, the electronic reader serves as companion technology that provides robust and quantitative measurements of device outputs. In some embodiments, the electronic reader comprises readily available consumer components, open-source code, and laser-cut acrylic housing, and is powered by a rechargeable lithium ion battery. The electronic reader can further comprise an onboard data storage unit. In some cases, to achieve sensitive detection of toehold switch signal output, an acrylic chip that holds the freeze-dried, paper-based reactions is placed into the reader between a light source (e.g., to read optical density at excitation and emission wavelengths of light appropriate for and characteristic of a particular detectable reporter) and electronic sensors. In some cases, the light source is a light emitting diode (LED) light source. Samples can be read using onboard electronics. In this manner, a portable electronic reader can provide low-noise measurements of changes associated with the reporter element including changes in light transmission due to LacZ-mediated color change.

In certain embodiments, provided herein is a device for identifying a pathogen-associated nucleic acid, comprising a preserved paper test article, wherein the methods described herein are performed using the preserved paper test article. In some cases, the paper test article is preserved by freeze-drying.

Articles of Manufacture

In another aspect, the present invention provides articles of manufacture useful for detecting a pathogen in a sample according to the methods provided herein. In certain embodiments, the article of manufacture is a kit for detecting Valley Fever, where the kit comprises a Valley Fever detecting agent, a plurality of preserved paper test articles as described herein, and an electronic optical reader. Optionally, a kit can further include instructions for performing the Valley Fever detection methods provided herein.

In certain embodiments, provided herein is a kit for detecting a Valley Fever-associated nucleic acid, where the kit comprises a plurality of preserved paper test articles, a Valley Fever detection agent, a plurality of toehold switches that encode at least a portion of a reporter protein and comprise one or more single-stranded toehold sequence domains that are complementary to a target Valley Fever nucleic acid or the reverse complement thereof, and an electronic optical reader. In some cases, the kit also comprises instructions for performing the Valley Fever detection methods provided herein.

In other embodiments, provided herein is a kit for detecting a Valley Fever-associated nucleic acid, where the kit comprises a plurality of preserved test tube test articles, a Valley Fever detection agent, a plurality of toehold switches that encode at least a portion of a reporter protein and comprise one or more single-stranded toehold sequence domains that are complementary to a Valley Fever pathogen nucleic acid or the reverse complement thereof, and an electronic optical reader. In some cases, the kit also comprises instructions for performing the Valley Fever detection methods provided herein.

In other embodiments, provided herein is a kit for detecting a Valley Fever-associated nucleic acid, where the kit comprises a plurality of preserved test tube test articles, a Valley Fever detection agent, a plurality of aptasensors that encode at least a portion of a reporter aptamer and comprise one or more single-stranded toehold sequence domains that are complementary to a Valley Fever pathogen nucleic acid or the reverse complement thereof, and an electronic optical reader. In some cases, the kit also comprises instructions for performing the Valley Fever detection methods provided herein.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

The present embodiments have been described in terms of one or more preferred embodiments, and it should be appreciated that many equivalents, alternatives, variations, and modifications, aside from those expressly stated, are possible and within the scope of the embodiments.

EXAMPLES

This section demonstrates rapid, low-cost, sensitive platforms for detection of Valley Fever. As illustrated in FIG. 1, the platforms use DNA and RNA extracted from patient serum samples.

Figures 4A, 4B:
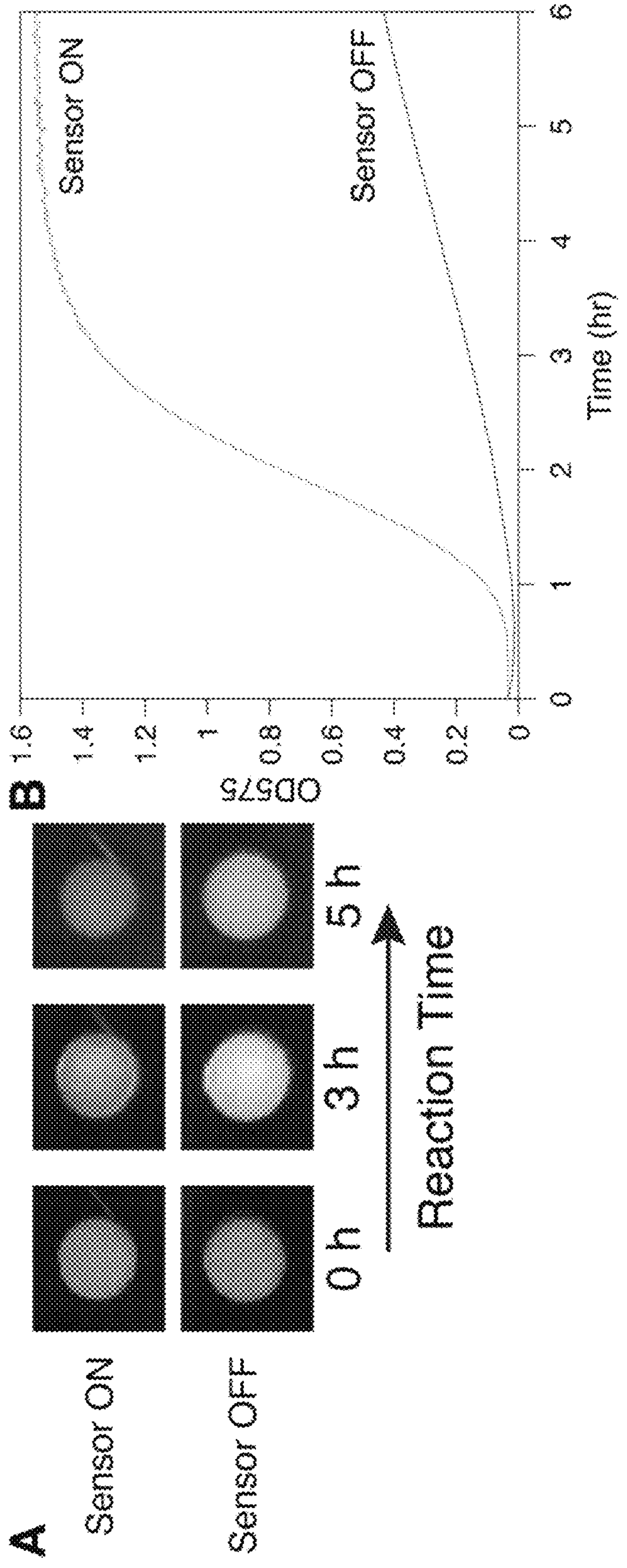
FIGS. 4A-4B present data validating use of a toehold switch sensor to detect nucleic acids from *Coccidioides posadasii*. (A) Photographs of the paper-based reactions for the toehold switch using the reporter beta-galactosidase as output. Over the 5-hour reaction, the paper device turns an obvious purple color in response to the Valley fever target RNA. A control reaction lacking the target RNA remains yellow over the course of the experiment. (B) Plate reader measurements of relative absorbance at 575 nm for the paper-based assay. The activated sensor with the Valley fever target RNA shows a substantial increase in absorbance, while a sensor tested in the absence of the target RNA remains markedly lower.

Toehold switches were designed to detect specific *Coccidioides posadasii* DNAs. Using these toehold switches, we developed sensors that enable direct visual detection of synthetic Valley fever DNA within hours (FIGS. 4A-4B). Sequences used for toehold switch Valley Fever diagnostic assays are provided in Table 1.

TABLE 1

Sequences Used for Toehold Switch Valley Fever Diagnostic

| Name | Nucleotide Sequence |
|---|---|
| Toehold switch VF sensor (RNA) | GGGCUGCACUCGCUUGACCGACUUCAAGUGCCACUGCUGGACUUUAG AACAGAGGAGAUAAAGAUGAGCAGUGGCACAACCUGGCGGCAGCGCA A (SEQ ID NO: 1) |
| RPA Forward Primer (DNA) | TCAACTAATACGACTCACTATAGGGCCTTCATTTCCATCTTCTCATCTTA TCCCATCCTTGG (SEQ ID NO: 2) |
| RPA Reverse Primer (DNA) | GAGAGGAACGAGAAGGACTCTTGGAATGCTA (SEQ ID NO: 3) |

Figures 5A, 5B:
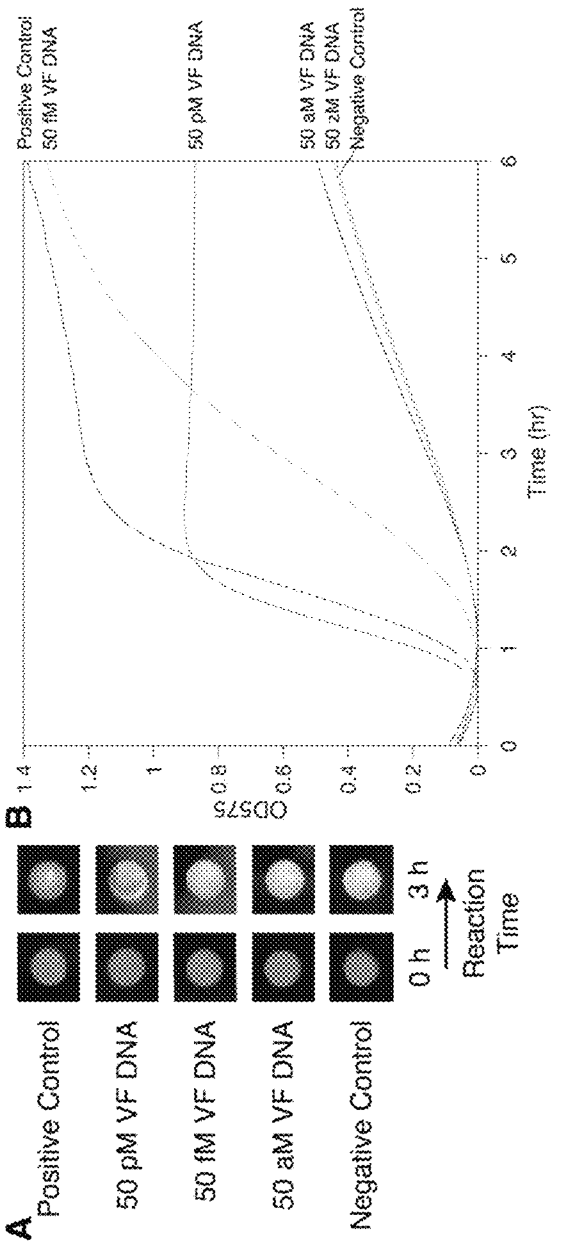
FIGS. 5A-5B present data validating a combined RPA and paper-based cell-free procedure for detection of lower concentrations of *Coccidioides posadasii* DNA. (A) Photographs of the paper-based reactions before and after incubation with RPA products produced from different concentrations of synthetic *C. posadasii* DNA. Concentrations down to 50 fM provide a discernable purple color compared to the negative control. (B) Plate reader measurements of the relative optical absorbance at 575 nm wavelength for a parallel set of paper-based reactions displayed in (A). Initial Valley fever DNA concentrations down to 50 fM can be readily distinguished. Experiments in this figure were performed by first amplifying the target DNA in RPA reactions over two hours. One of the amplification primers was used to append a T7 RNA polymerase sequence to the amplicon. The amplified DNA was then diluted with water and applied to paper-based assays with the *C. posadasii* specific toehold switch. During these reactions, the amplified DNA was transcribed into RNA using T7 RNA polymerase to activate the toehold switch.

The isothermal amplification method Recombinase Polymerase Amplification (RPA) was used with RPA forward and reverse primers (Table 1) to amplify DNA sequences. The RPA amplification products were added to paper-based cell-free reactions containing the VF-specific toehold switches, which provide a visual reaction readout. As shown in FIGS. 5A-5B, the data revealed that an RPA reaction followed by toehold switch detection enables identification of Valley fever DNA down to concentrations of at least 50 fM.

Figures 6A, 6B:
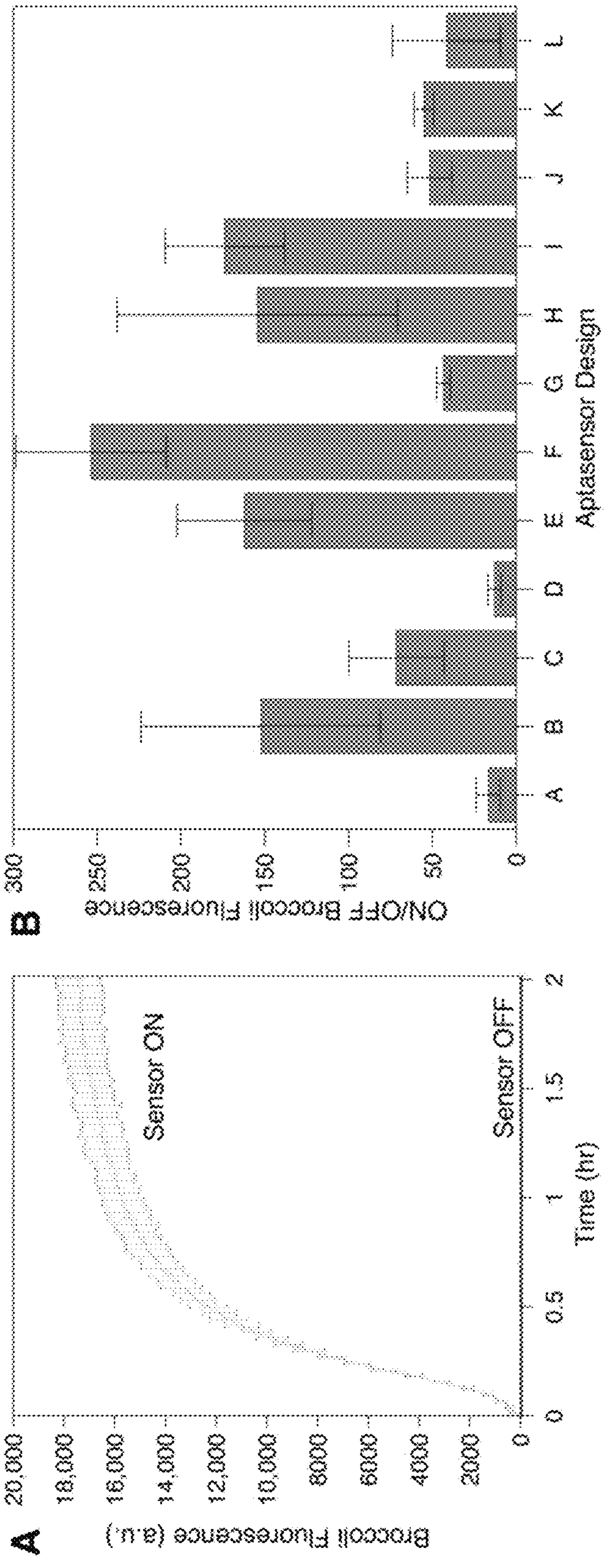
FIGS. 6A-6B present data validating use of multiple Broccoli aptasensors to target *Coccidioides posadasii* DNA. (A) A time-course measurement of Broccoli aptasensor F in the presence of transcribed *C. posadasii* RNA target. Over 200-fold increase in Broccoli fluorescence in the presence of the Valley fever nucleic acid is observed due to high sensor ON state fluorescence and very low OFF state fluorescence. (B) Characterization of a library of 12 Broccoli aptasensors designed to detect the same RNA fragment from the *C. posadasii* genome. Five aptasensors, including F from panel (A), provide over 100-fold increases in signal upon detection of the target RNA

We designed a library of Broccoli aptasensors targeting the same *Coccidioides posadasii* nucleic acids and evaluated them for sensitivity. Sequences used for Broccoli aptamer Valley Fever diagnostic assays are provided in Table 2. As shown in FIGS. 6A-6B, multiple aptasensor designs provided at a 100-fold increase in fluorescence upon activation.

Figures 7A, 7B:
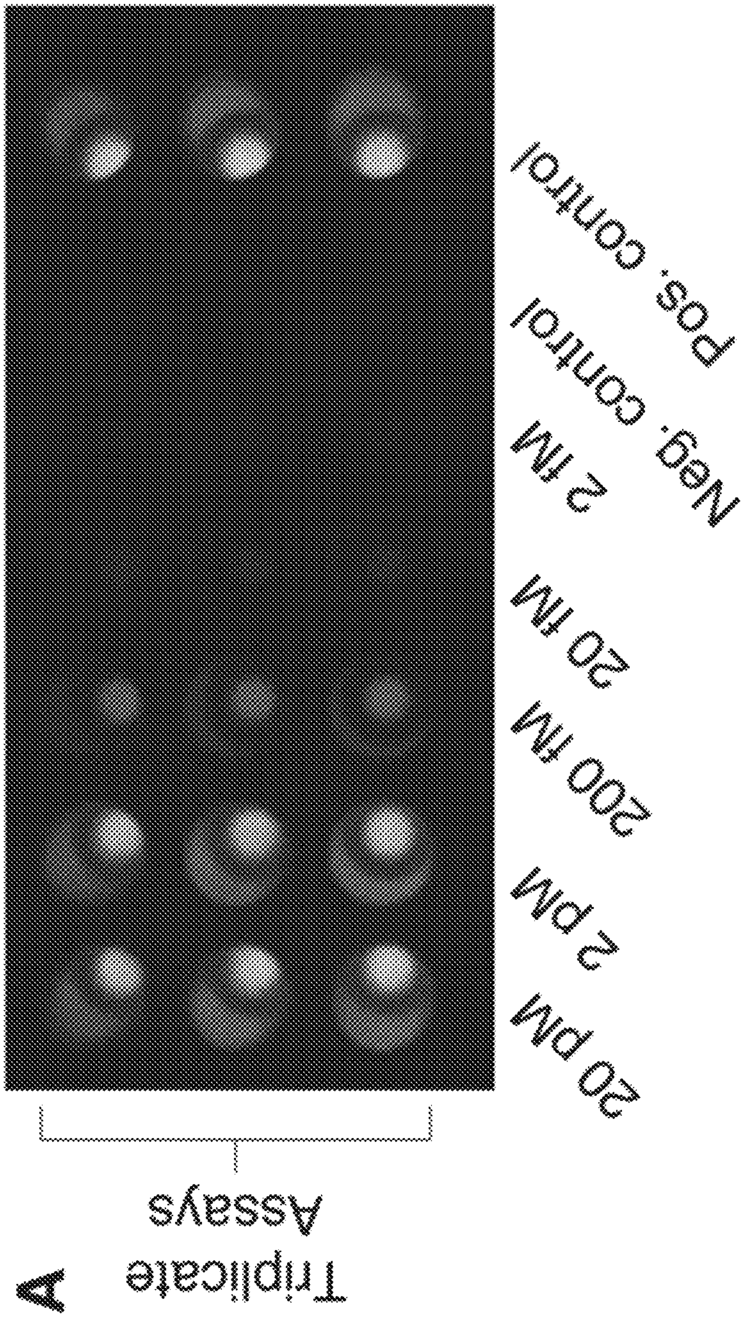
FIGS. 7A-7B present data validating the use of RPA and Broccoli aptasensors for detection of low concentrations of *Coccidioides posadasii* target DNA. (A) Photograph of the final assays run using different concentrations of target DNA. Concentrations down to 20 fM can be identified by eye upon illumination by a blue light source with a long pass optical filter. Reactions were run in triplicate for each column of wells. (B) Plate reader measurements of Broccoli fluorescence for the assay using different starting concentrations of the target DNA. Quantitative plate reader measurements enable detection of *C. posadasii* DNA down to concentrations of at least 2 fM. The assays in this figure were run by first amplifying the synthetic Valley fever target DNA in 2-hour RPA reactions. During amplification, one of the primers was used to add a T7 RNA polymerase promoter site to the resulting amplicon. The amplified DNA products were then directly added to an in vitro transcription reaction with T7 RNA polymerase, the DNA template for the Broccoli aptasensor, and the Broccoli chromophore DFHBI-1T. Plate reader measurements commenced 20 minutes after the start of in vitro transcription.
Figures 7A, 7B:
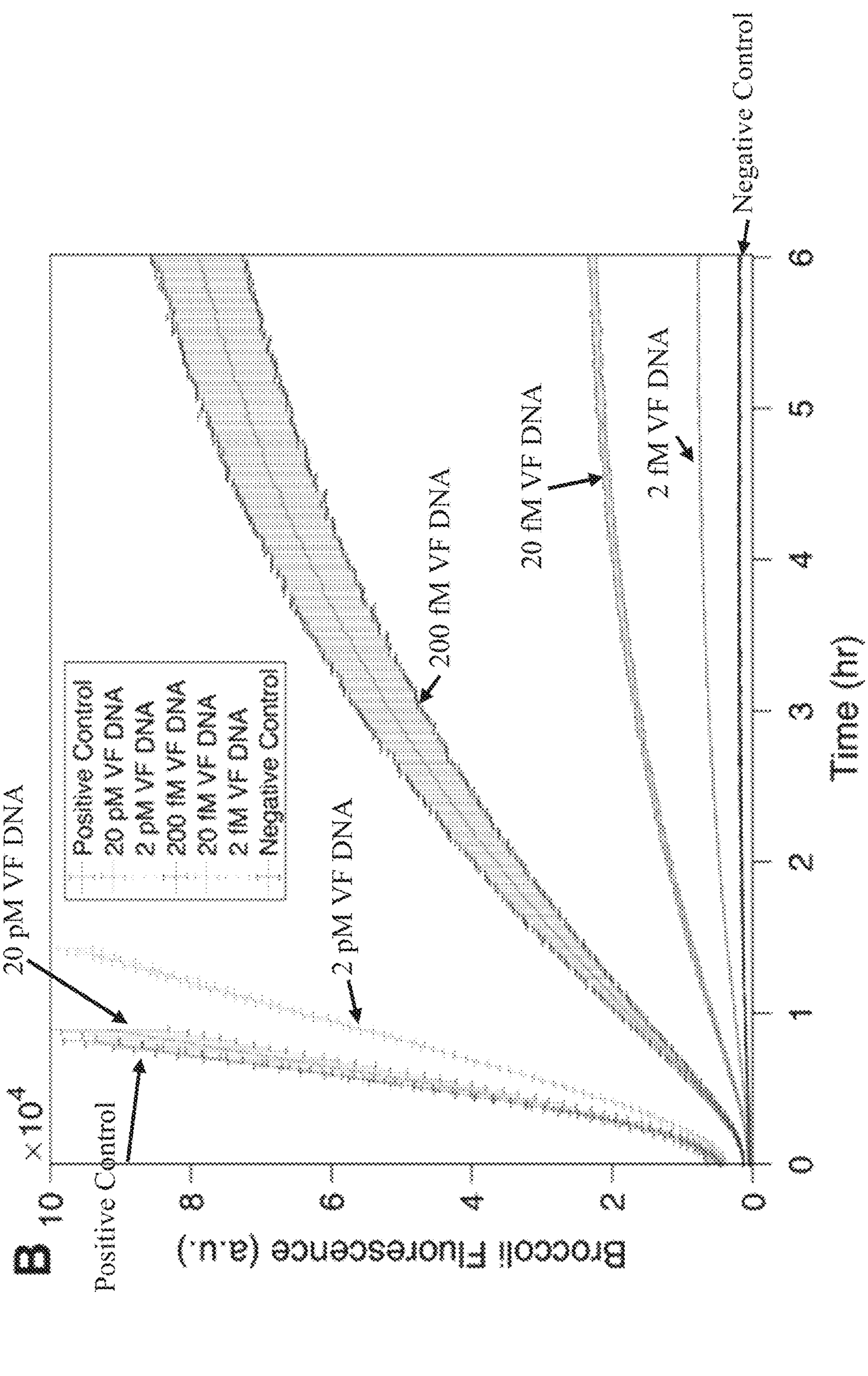

As shown in FIG. 7A, two-pot reactions using RPA for amplification and Broccoli aptasensors for detection enable readout by eye down to 20 fM. Using a plate reader enabled detection down to at least 2 fM. See FIG. 7B.

The experiments and data described herein demonstrate development and use of paper-based assays for detection of Valley Fever nucleic acids that do not require expensive thermal cycling equipment, provide test results that can be read directly by eye, and employ toehold switch riboregulators to eliminate false positives caused by non-specific amplification. Toehold switches and Broccoli aptasensors for detection of Valley fever have been validated using synthetic DNA samples. When coupled with isothermal amplification via RPA, these toehold switches and aptasensors enable simple visual detection of Valley fever DNA down to at least 50 fM and 20 fM, respectively. We expect that further optimization of amplification primers and sensors will enable additional improvements in assay sensitivity. One-pot reactions that combine isothermal amplification and detection using Broccoli aptasensors have the potential to substantially decrease assay time and complexity.

TABLE 2

Sequences Used for Broccoli Aptasensor Valley Fever Diagnostic

| Aptasensor Name | Aptasensor Sequence |
|---|---|
| Toehold switch VF sensor | GGGCUGCACUCGCUUGACCGACUUCAAGUGCCACUGCUGGACUUU AGAACAGAGGAGAUAAAGAUGAGCAGUGGCACAACCUGGCGGCA GCGCAA (SEQ ID NO: 1) |
| Broccoli Aptasensor A | GGGUCUCGGCAACGAUGGCUGCACUCGCUUGACCGACUGACCAUA AAGUAGGUGAAGCGAGUGCAGUCGAGUAGAGUGUGGGCUCAGAU UCGUCUGAGACGGUCGGGUCCUGCACUAGCAUAACCCCUUGGGGC (SEQ ID NO: 4) |
| Broccoli Aptasensor B | GGGACUGCUUCGUUGAGGCUCUCGGCAACGAUGGCUGCUAACAC UCGCAUCCACCGUUGCCGAGAGUCGAGUAGAGUGUGGGCUCAGA UUCGUCUGAGACGGUCGGGUCCUCUCGGUAGCAUAACCCCUUGGG GC (SEQ ID NO: 5) |
| Broccoli Aptasensor C | GGGGGCAACGAUGGCUGCACUCGCUUGACCGACUUCAAAUCAGAC CUUGCAGUAGGUCAAGCGAGUUCGAGUAGAGUGUGGGCUCAGAU UCGUCUGAGACGGUCGGGUCACUCGCUUAGCAUAACCCCUUGGGG C (SEQ ID NO: 6) |
| Broccoli Aptasensor D | GGGGAGGCUCUCGGCAACGAUGGCUGCACUCGCUUGACCCCGAAU UGUCUAGCAAGUGCAGCCAUCUCGAGUAGAGUGUGGGCUCAGAU UCGUCUGAGACGGUCGGGUCGAUGGCUGUAGCAUAACCCCUUGG GGC (SEQ ID NO: 7) |
| Broccoli Aptasensor E | GGGACUGCUUCGUUGAGGCUCUCGGCAACGAUGGCUGCUUAACU ACGCAUCCACCGUUGCCGAGAGUCGAGUAGAGUGUGGGCUCAGA UUCGUCUGAGACGGUCGGGUCCUCUCGGCUAGCAUAACCCCUUGG GGC (SEQ ID NO: 8) |
| Broccoli Aptasensor F | GGGGCAACGAUGGCUGCACUCGCUUGACCGACUUCAAGAACGUCA CCUUAAAGCCGGUCAAGCGAGUCGAGUAGAGUGUGGGCUCAGAU UCGUCUGAGACGGUCGGGUCCUCGCUUGAUAGCAUAACCCCUUGG GGC (SEQ ID NO: 9) |

TABLE 2-continued

Sequences Used for Broccoli Aptasensor Valley Fever Diagnostic

| Aptasensor Name | Aptasensor Sequence |
|---|---|
| Broccoli Aptasensor G | GGGGGCAACGAUGGCUGCACUCGCUUGACCGACUUCAAGCCCUCA AUUGUAGUAGGUCAAGCGAGUUCGAGUAGAGUGUGGGCUCAGAU UCGUCUGAGACGGUCGGGUCACUCGCUUGUAGCAUAACCCCUUGG GGC (SEQ ID NO: 10) |
| Broccoli Aptasensor H | GGGUGUAAGUGAAGCGACACCAAAUUCUUGCAUCUCGCUUAUUG UCGCGUGAUACAAGAAUUUGGUUCGAGUAGAGUGUGGGCUCAGA UUCGUCUGAGACGGUCGGGUCACCAAAUUCUAGCAUAACCCCUUG GGGC (SEQ ID NO: 11) |
| Broccoli Aptasensor I | GGGAUCUGUAAGUGAAGCGACACCAAAUUCUUGCAUCUGGCGUU AAAGACGCAUGAAUUUGGUGUCUCGAGUAGAGUGUGGGCUCAGA UUCGUCUGAGACGGUCGGGUCGACACCAAAUAGCAUAACC CUUG GGGC (SEQ ID NO: 12) |
| Broccoli Aptasensor J | GGGGCAACGAUGGCUGCACUCGCUUGACCGACUUCAAGAACUGCG CCUUAAAGCCGGUCAAGCGAGUCGAGUAGAGUGUGGGCUCAGAU UCGUCUGAGACGGUCGGGUCCUCGCUUGACUAGCAUAACCCCUUG GGGC (SEQ ID NO: 13) |
| Broccoli Aptasensor K | GGGGGCAACGAUGGCUGCACUCGCUUGACCGACUUCAAGGCCGUA AUUGCAGUAGGUCAAGCGAGUUCGAGUAGAGUGUGGGCUCAGAU UCGUCUGAGACGGUCGGGUCACUCGCUUGAUAGCAUAACCCCUUG GGGC (SEQ ID NO: 14) |
| Broccoli Aptasensor L | GGGUCUCGGCAACGAUGGCUGCACUCGCUUGACCGACUGCCUCAU AAGUAGGUGAAGCGAGUGCAGUCGAGUAGAGUGUGGGCUCAGAU UCGUCUGAGACGGUCGGGUCCUGCACUCGCUAGCAUAACCCCUUG GGGC (SEQ ID NO: 15) |
| RPA Forward Primer | AATTCTAATACGACTCACTATAGGGAGAAGGTTTCCATCTTCTCATC TTATCCCATCCTTGG (SEQ ID NO: 16) |
| RPA Reverse Primer | GAGAGGAACGAGAAGGACTCTTGGAATGCTA (SEQ ID NO: 3) |

We claim:

1. A method of detecting a target nucleic acid in a sample, the method comprising the steps of:

(a) amplifying nucleic acids obtained from a biological sample of a subject, wherein amplifying comprises isothermal amplification;

(b) contacting the amplified nucleic acid to a toehold switch, wherein the toehold switch encodes at least a portion of a reporter protein and comprises one or more single-stranded toehold sequence domains that are complementary to a target *Coccidioides immitis* or *Coccidioides posadasii* nucleic acid, or the reverse complement thereof, wherein the contacting occurs under conditions that allow translation of the coding domain in the presence of the target nucleic acid but not in the absence of the target nucleic acid; and (c) detecting the reporter protein as an indicator that the target *Coccidioides immitis* or *Coccidioides posadasii* nucleic acid is present in the amplified nucleic acids.

2. The method of claim 1, wherein the target nucleic acid is detectable at a concentration as low as 2 fM.

3. The method of claim 1, wherein the reporter protein, if present, is detectable in less than 4 hours.

4. The method of claim 1, wherein the reporter protein, if present, is detectable in less than 2 hours.

5. The method of claim 1, wherein the isothermal amplification is a method selected from the group consisting of NASBA, LAMP, and RPA.

6. The method of claim 1, wherein the toehold switch comprises SEQ ID NO:1.

7. A method of detecting presence of pathogen specific nucleic acid in a sample, the method comprising the steps of:

(a) amplifying nucleic acids obtained from a biological sample of a subject, wherein amplifying comprises isothermal amplification; and (b) contacting the amplified nucleic acids to an aptamer-based sensor, wherein the aptamer-based sensor is a nucleic acid sequence comprising one or more single-stranded toehold sequence domains that are complementary to the target *Coccidioides immitis* or *Coccidioides posadasii* nucleic acid, a fully or partially double-stranded stem domain, a loop domain, and an aptamer-ligand complex, and wherein the contacting occurs under conditions that promote activation of the aptamer-ligand complex in the presence of the target *Coccidioides immitis* or *Coccidioides posadasii* nucleic acid but not in the absence of the *Coccidioides immitis* or *Coccidioides posadasii* associated nucleic acid.

8. The method of claim 7, wherein the aptamer-ligand complex comprises a fluorescent aptamer selected from the group consisting of Broccoli, Spinach2, Carrot, Radish, a G-quadruplex-containing aptamer, and a malachite green binding aptamer.

9. The method of claim 8, wherein fluorescence, if present, is detectable in less than 4 hours.

10. The method of claim 8, wherein fluorescence, if present, is detectable in less than 2 hours.

11. The method of claim 7, wherein the isothermal amplification is a method selected from the group consisting of NASBA, LAMP, and RPA.

12. The method of claim 6, wherein the target nucleic acid is detectable at a concentration as low as 2 fM.

13. A synthetic toehold switch sensor comprising a fully or partially double-stranded stem domain, a loop domain, a toehold domain, and at least a portion of a coding sequence of a reporter gene, wherein the toehold domain and at least a portion of the stem domain are complementary to a target *Coccidioides immitis* and/or *Coccidioides posadasii* RNA sequence.

14. The toehold switch sensor of claim 13, comprising a RNA sequence of SEQ ID NO:1.

* * * * *

UNITED STATES PATENT AND TRADEMARK OFFICE

CERTIFICATE OF CORRECTION

PATENT NO. : 11,214,841 B2
APPLICATION NO. : 16/294578
DATED : January 4, 2022
INVENTOR(S) : Alexander Green It is certified that error appears in the above-identified patent and that said Letters Patent is hereby corrected as shown below:

In the Claims

Column 23, Claim 7, Line 11, "*posadasii* associated nucleic" should be -- *posadasii* nucleic --.

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 16

<210> SEQ ID NO 1
<211> LENGTH: 95
<212> TYPE: RNA
<213> ORGANISM: Artificial Sequence
<220> FEATURE:
<223> OTHER INFORMATION: toehold switch VF sensor

<400> SEQUENCE: 1
gggcugcacu cgcuugaccg acuucaagug ccacugcugg acuuuagaac agaggagaua 60
aagaugagca guggcacaac cuggcggcag cgcaa 95

<210> SEQ ID NO 2
<211> LENGTH: 62
<212> TYPE: DNA
<213> ORGANISM: Artificial Sequence
<220> FEATURE:
<223> OTHER INFORMATION: RPA forward primer

<400> SEQUENCE: 2
tcaactaata cgactcacta tagggccttc atttccatct tctcatctta tcccatcctt 60
gg 62

<210> SEQ ID NO 3
<211> LENGTH: 31
<212> TYPE: DNA

<213> ORGANISM: Artificial Sequence
<220> FEATURE:
<223> OTHER INFORMATION: RPA reverse primer

<400> SEQUENCE: 3
gagaggaacg agaaggactc ttggaatgct a 31

<210> SEQ ID NO 4
<211> LENGTH: 134
<212> TYPE: RNA
<213> ORGANISM: Artificial Sequence
<220> FEATURE:
<223> OTHER INFORMATION: Broccoli aptasensor A

<400> SEQUENCE: 4
gggucucggc aacgauggcu gcacucgcuu gaccgacuga ccauaaagua ggugaagcga 60
gugcagucga guagagugug ggcucagauu cgucugagac ggucgggucc ugcacuagca 120
uaaccccuug gggc 134

<210> SEQ ID NO 5
<211> LENGTH: 135
<212> TYPE: RNA
<213> ORGANISM: Artificial Sequence
<220> FEATURE:
<223> OTHER INFORMATION: Broccoli aptasensor B

<400> SEQUENCE: 5
gggacugcuu cguugaggcu cucggcaacg auggcugcua acacucgcau ccaccguugc 60
cgagagucga guagagugug ggcucagauu cgucugagac ggucgggucc ucucgguagc 120
auaaccccuu ggggc 135

<210> SEQ ID NO 6
<211> LENGTH: 135
<212> TYPE: RNA
<213> ORGANISM: Artificial Sequence
<220> FEATURE:
<223> OTHER INFORMATION: Broccoli aptasensor C

<400> SEQUENCE: 6
gggggcaacg auggcugcac ucgcuugacc gacuucaaau cagaccuugc aguaggucaa 60
gcgaguucga guagagugug ggcucagauu cgucugagac ggucggguca cucgcuuagc 120
auaaccccuu ggggc 135

<210> SEQ ID NO 7
<211> LENGTH: 136
<212> TYPE: RNA
<213> ORGANISM: Artificial Sequence
<220> FEATURE:
<223> OTHER INFORMATION: Broccoli aptasensor D

<400> SEQUENCE: 7
ggggaggcuc ucggcaacga uggcugcacu cgcuugaccc cgaauugucu agcaagugca 60
gccaucucga guagagugug ggcucagauu cgucugagac ggucgggucg auggcuguag 120
cauaaccccu uggggc 136

<210> SEQ ID NO 8
<211> LENGTH: 136
<212> TYPE: RNA
<213> ORGANISM: Artificial Sequence
<220> FEATURE:
<223> OTHER INFORMATION: Broccoli aptasensor E

<400> SEQUENCE: 8
gggacugcuu cguugaggcu cucggcaacg auggcugcuu aacuacgcau ccaccguugc 60
cgagagucga guagagugug ggcucagauu cgucugagac ggucgggucc ucucggcuag 120
cauaaccccu uggggc 136

<210> SEQ ID NO 9
<211> LENGTH: 137
<212> TYPE: RNA
<213> ORGANISM: Artificial Sequence
<220> FEATURE:
<223> OTHER INFORMATION: Broccoli aptasensor F

<400> SEQUENCE: 9
ggggcaacga uggcugcacu cgcuugaccg acuucaagaa cgucaccuua aagccgguca 60
agcgagucga guagagugug ggcucagauu cgucugagac ggucgggucc ucgcuugaua 120
gcauaacccc uuggggc 137

<210> SEQ ID NO 10
<211> LENGTH: 137
<212> TYPE: RNA
<213> ORGANISM: Artificial Sequence
<220> FEATURE:
<223> OTHER INFORMATION: Broccoli aptasensor G

<400> SEQUENCE: 10
gggggcaacg auggcugcac ucgcuugacc gacuucaagc ccucaauugu aguaggucaa 60
gcgaguucga guagagugug ggcucagauu cgucugagac ggucggguca cucgcuugua 120
gcauaacccc uuggggc 137

<210> SEQ ID NO 11
<211> LENGTH: 137
<212> TYPE: RNA
<213> ORGANISM: Artificial Sequence
<220> FEATURE:
<223> OTHER INFORMATION: Broccoli aptasensor H

<400> SEQUENCE: 11
ggguguaagu gaagcgacac caaauucuug caucucgcuu auugucgcgu gauacaagaa 60
uuugguucga guagagugug ggcucagauu cgucugagac ggucggguca ccaaauucua 120
gcauaacccc uuggggc 137

<210> SEQ ID NO 12
<211> LENGTH: 137
<212> TYPE: RNA
<213> ORGANISM: Artificial Sequence
<220> FEATURE:
<223> OTHER INFORMATION: Broccoli aptasensor I

<400> SEQUENCE: 12
gggaucugua agugaagcga caccaaauuc uugcaucugg cguuaaagac gcaugaauuu 60
ggugucucga guagagugug ggcucagauu cgucugagac ggucgggucg acaccaaaua 120
gcauaacccc uuggggc 137

<210> SEQ ID NO 13
<211> LENGTH: 138
<212> TYPE: RNA
<213> ORGANISM: Artificial Sequence
<220> FEATURE:

-continued

```
<223> OTHER INFORMATION: Broccoli aptasensor J

<400> SEQUENCE: 13

ggggcaacga uggcugcacu cgcuugaccg acuucaagaa cugcgccuua aagccgguca      60

agcgagucga guagagugug ggcucagauu cgucugagac ggucgggucc ucgcuugacu     120

agcauaaccc cuuggggc                                                   138


<210> SEQ ID NO 14
<211> LENGTH: 138
<212> TYPE: RNA
<213> ORGANISM: Artificial Sequence
<220> FEATURE:
<223> OTHER INFORMATION: Broccoli aptasensor K

<400> SEQUENCE: 14

gggggcaacg auggcugcac ucgcuugacc gacuucaagg ccguaauugc aguaggucaa      60

gcgaguucga guagagugug ggcucagauu cgucugagac ggucggguca cucgcuugau     120

agcauaaccc cuuggggc                                                   138


<210> SEQ ID NO 15
<211> LENGTH: 138
<212> TYPE: RNA
<213> ORGANISM: Artificial Sequence
<220> FEATURE:
<223> OTHER INFORMATION: Broccoli aptasensor L

<400> SEQUENCE: 15

gggucucggc aacgauggcu gcacucgcuu gaccgacugc cucauaagua ggugaagcga      60

gugcagucga guagagugug ggcucagauu cgucugagac ggucgggucc ugcacucgcu     120

agcauaaccc cuuggggc                                                   138


<210> SEQ ID NO 16
<211> LENGTH: 62
<212> TYPE: DNA
<213> ORGANISM: Artificial Sequence
<220> FEATURE:
<223> OTHER INFORMATION: forward primer

<400> SEQUENCE: 16

aattctaata cgactcacta tagggagaag gtttccatct tctcatctta tcccatcctt      60

gg                                                                     62
```